United States Patent [19]

Schmitz et al.

[11] 4,302,470
[45] Nov. 24, 1981

[54] ACANTHIFOLIC ACID—NEW ANTI-TUMOR AND ANTIBIOTIC AGENT

[75] Inventors: Francis J. Schmitz; Dick van der Helm; M. Bilayet Hossain; Yalamanchili Gopichand, all of Norman, Okla.; Ravi S. Prasad, Riverdale, Md.

[73] Assignee: Research Corporation, New York, N.Y.

[21] Appl. No.: 170,927

[22] Filed: Jul. 21, 1980

[51] Int. Cl.$^3$ ............................................ C07D 407/14
[52] U.S. Cl. ..................................... 424/283; 542/401
[58] Field of Search ........................ 542/401; 424/283; 549/90

[56] References Cited

U.S. PATENT DOCUMENTS 4,218,443  8/1980  Comai et al. .......................... 424/283
4,221,724  9/1980  Liv et al. .............................. 424/283

OTHER PUBLICATIONS

Westley Advances in Applied Microbiology 22(1977) pp. 177-223.
Sharma et al. Transactions of the Drugs from the Sea Symposium, Univ. Rhode Island, 1967.

Primary Examiner—Arthur P. Demers
Attorney, Agent, or Firm—Oblon, Fisher, Spivak, McClelland & Maier

[57] ABSTRACT

A purified bioactive compound of the formula:

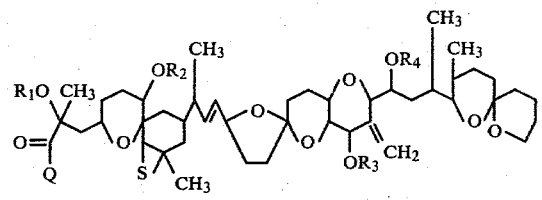

wherein:
Q is selected from the group consisting of OY and $NZ_1Z_2$;
Y is selected from the group consisting of H, alkyl, hydroxyalkyl, aminoalkyl, substituted aminoalkyl, aryl and a pharmaceutically acceptable cation;
$Z_1$ and $Z_2$ are selected from the group consisting of H, alkyl, hydroxyalkyl, aminoalkyl, substituted aminoalkyl and aryl;
$R_1$, $R_2$, $R_3$ and $R_4$ are selected from the group consisting of H, alkyl, hydroxyalkyl, aminoalkyl, substituted aminoalkyl, aryl and

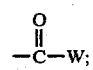

and
W is selected from the group consisting of H, alkyl, hydroxyalkyl, aminoalkyl, substituted aminoalkyl and aryl.

6 Claims, 3 Drawing Figures

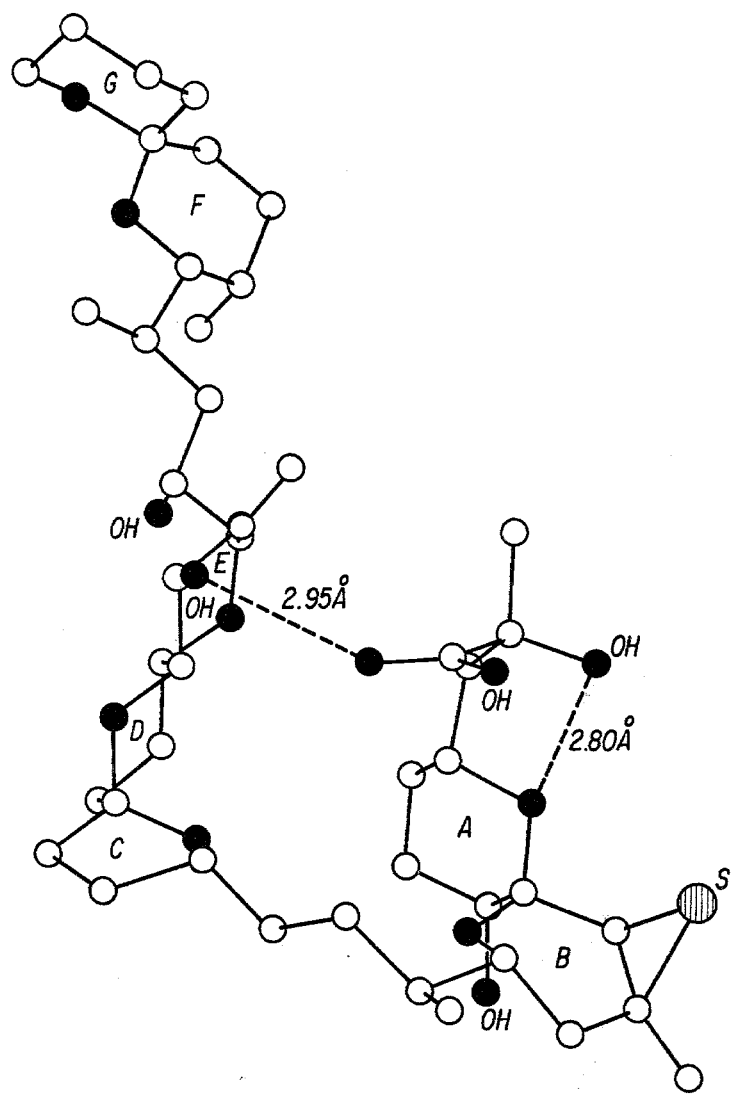
FIG. 3 ACANTHIFOLIC ACID
● OXYGEN
○ CARBON
---- HYDROGEN BONDS

ACANTHIFOLIC ACID—NEW ANTI-TUMOR AND ANTIBIOTIC AGENT

BACKGROUND OF THE INVENTION

The invention described herein was made in the course of work under a grant or award from the Department of Health, Education and Welfare.

FIELD OF THE INVENTION

This invention relates generally to bioactive compounds and particularly to such compounds which are derived from certain marine sponges.

DESCRIPTION OF THE PRIOR ART

A number of bioactive natural products are derived from extracts of plants or micoorganisms. One area of interest has been the development of new antineoplastic compounds for clinical use to combat cancer.

Typically, a two-step strategy has been employed in the search for such new agents: (a) random screening of large numbers of plant extracts; and (b) in-depth isolation studies on the small percentage of extracts found to be active. The underlying assumption in this approach is that plant extracts possessing a demonstrated potential usefulness, using the best available bioassays, are the logical starting point for isolating new anticancer agents. This approach has yielded many active compounds, but only a small fraction of these are now in use clinically or at an advanced stage for clinical evaluation.

Although this strategy has been utilized for nearly 20 years to derive antineoplastic agents from terrestrial sources, it has only recently been applied to marine organisms. Approximately 6,000 marine animal species have been tested to date in a National Institute of Cancer screening program in which approximately 5% have shown confirmed activity. This is an extremely small number compared to the 100,000 terrestrial plant species tested.

Although the number of antineoplastic agents reported from marine sources is still quite small, the variety of classes of compounds isolated is great. Active agents from marine organisms include halogenated sesquiterpenes, diterpenoids, alkaloids, triterpene glycosides and high molecular weight proteins.

Many types of marine algae, invertebrates and vertebrates have been examined, see for example G. R. Pettit et al, Nature, 227, 962 (1970) and A. J. Weinheimer et al, Proceedings of the Food-Drugs from the Sea Symposium, 1974, Marine Technology Society, Washington, D.C., p. 491–496. Among the marine invertebrates, sponges have been considered as sources of antitumor compounds. Crude extracts from marine sponges of the species Verongia fistularis and Verongia cauliformis, for example, have been found to contain antitumor activity. Four compounds have been isolated from the crude extracts with melting points of 195°, 191°, 137° and 132° C., but it is not clear which of these compounds possess cytotoxic activity, see Sharma et al, Transactions of the Drugs from the Sea Symposium, University of Rhode Island, p. 119–126, 1967 (published 1968); Chem. Abst. 70, 45171 t (1969) and 72, 76126 c (1970). Gopichand and Schmitz have isolated and identified one of the cytotoxic compounds present in the extracts of V. fistularis [Y. Copichand et al, Tetra. Letters, 3921–3924 (1974)].

Other common sources of natural bioactive compounds are microorganisms. For example, the compounds referred to as polyether antibiotics are generally obtained from microorganisms and possess some structural similarities to the subject compounds of the present invention. Polyether antibiotics have been obtained from microorganisms such as Streptomyces species cinnamonensis, eurocidus, violaceoniger, sp. X-464, hygroscopicus, isolate A158, albus, griseus, aureofaciens, ribosidificus and X-206.

This class of compounds has been reviewed by Westley in Advances in Applied Microbiology, 22, 177 (1977). Of the various classes of polyether antiobiotics, the compounds of the present invention most resemble those referred to as monovalent polyethers, Class 1a, by Westley in his review article at page 185.

Polyether antibiotics have been found to be useful as general antibiotics with specific applications in treatment of poultry coccidiosis, stimulating myocardial contractility, and improving the utilization of ruminant feed.

Marine organisms are the source of unusual toxins, halogenated compounds and sterols not encountered in terrestrial organisms. Apparently, life forms that have remained in the ocean retain biosynthetic capabilities that are not shared by terrestrial organisms. Marine organisms, such as sponges, thus constitute a unique, vast and heretofore untapped resource for discovering unique bioactive molecules.

SUMMARY OF THE INVENTION

Accordingly, it is one object of the present invention to provide novel cytotoxic, tumor-inhibitory, and antibiotic compounds.

A further object of the present invention is to provide compounds which stimulate myocardial contractility and improve the utilization of ruminant feed.

A further object of the present invention is to provide compounds which are effective in treating poultry coccidiosis.

A further object of the present invention is to extract and identify bioactive compounds from marine sponges.

These and other objects of the present invention as will be understood by the following description have been attained by providing acanthifolic acid and derivatives thereof in purified form with the formula:

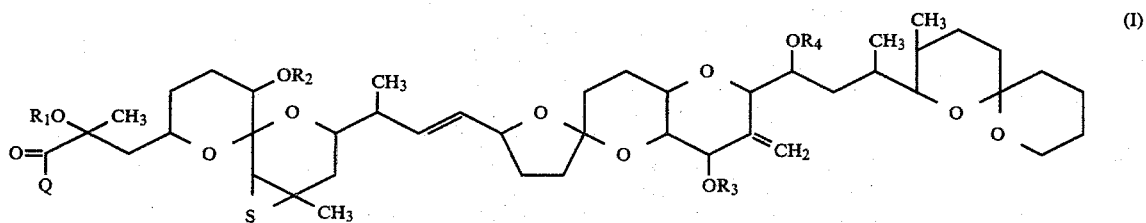

wherein Q is selected from the group consisting of OY and $NZ_1Z_2$;

Y is selected from the group consisting of H, alkyl, aryl and a pharmaceutically acceptable cation; $Z_1$ and $Z_2$ are independently selected from the group consisting of H, alkyl and aryl;

$R_1$, $R_2$, $R_3$ and $R_4$ are independently selected from the group consisting of H, alykl, aryl, and

; and

W is selected from the group consisting of H, alkyl and aryl.

BRIEF DESCRIPTION OF THE DRAWINGS

A more complete appreciation of the invention and many of the attendant advantages thereof will be readily attained as the same becomes better understood by reference to the following detailed description when considered in connection with the accompanying drawings, wherein:

FIG. 3 shows a perspective view of the structure of acanthifolic acid.

DETAILED DESCRIPTION OF THE PREFERRED EMBODIMENTS

Isolation

Figure 1:
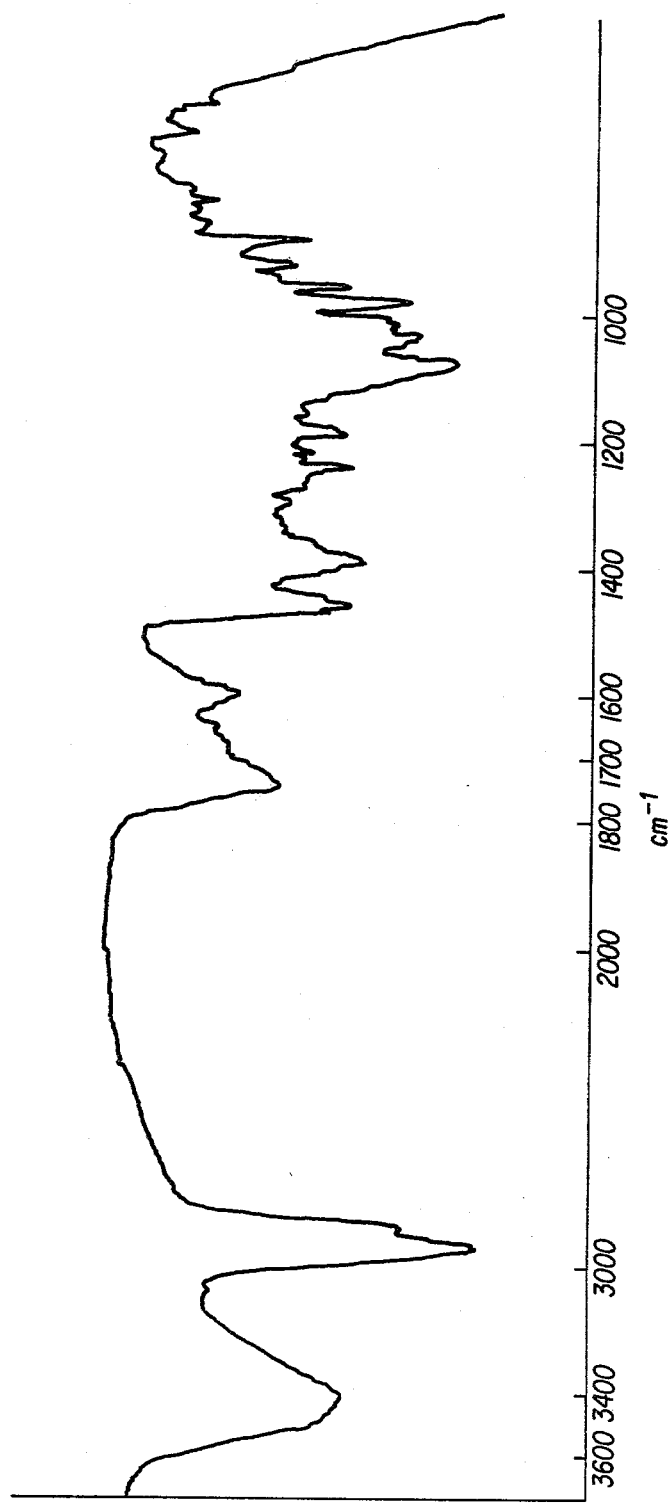
FIG. 1 is an infrared spectrum of acanthifolic acid.

The parent compound of the present invention is named "acanthifolic acid" and has the following structure:

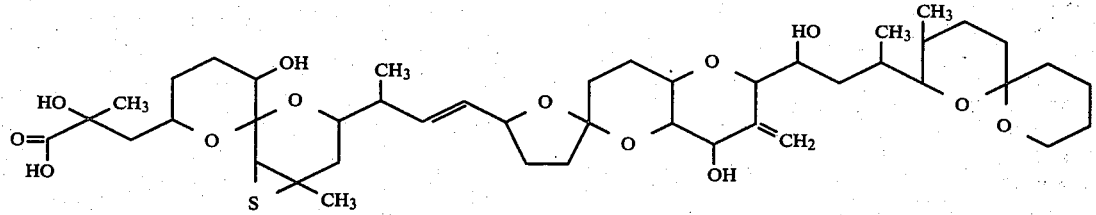

Acanthifolic acid may be synthesized or may be isolated from sponges such as the species *Tedanis ignis, Xestospongia longleyi, Anthosigmella varians, Verongia spengelii, Thorectopsamma chromogenia, Xestospongia muta,* or *Halichondria melanodocia,* or from the genus Pandaros such as *Pandaros acanthifolium.* Acanthifolic acid may also be extracted from algae or from microorganisms living within marine sponges.

The sponges from which acanthifolic acid is isolated are usually collected by hand, but may also be obtained by other methods, such as dredging or with a suitable submersible vessel.

In order to obtain workable quantities of acanthifolic acid, approximately 1 to 100 pounds of the sponges are cut into pieces of a size which allows thorough and convenient extraction. Suitable convenient sizes include about 1 mm² to about 5 in². This laboratory procedure may be further scaled up in order to process a greater amount of sponges.

After being cut, the sponges can be used immediately or preserved in a suitable medium. The preserving and/or extracting medium may be common organic solvents. Suitable solvents include alcohols such as ethyl alcohol, isopropyl alcohol, acetone or mixtures of these with chloroform, benzene or ethyl acetate.

The sponge extracts are fractionated by solvent partitioning in order to obtain fractions differing substantially in polarity. These fractions may be further purified to obtain pure compounds. By "purified" material is meant at least 90 to 95% acanthifolic acid, and preferably more than 99% acanthifolic acid.

The pertinent fraction may be obtained by extraction of the concentrated crude extract (usually diluted with some water) with a solvent such as an alkane, methylene chloride, chloroform, carbon tetrachloride, ethyl acetate, benzene or a mixture thereof, applied either in combinations or sequentially. Generally, any low molecular weight, volatile, somewhat polar, water-immiscible solvent or mixture of solvents would be suitable. Suitable alkanes include pentane, hexane, heptane, isooctane or mixtures thereof.

The organic solubles from such an extraction may be subjected to a series of solvent partitions to further concentrate acanthifolic acid. This may be done by dissolving these organic solubles in methanol-water (approximately 9:1) and partitioning the resulting solution successively against hexane, carbon tetrachloride, and chlororform, the water content in the methanol phase being increased after the hexane and carbon tetrachloride extractions to give methanol-water mixtures of approximately 8:2 and 7:3, respectively. Other water soluble alcohols or a different series of increasingly polar water-immiscible organic solvents may be used.

The initial extraction and subsequent ones may be effected by percolation, Soxhlet extraction, continuous liquid-liquid extraction, or counter-current extraction (solvent partitioning). The final separation of the compound is accomplished by conventional chromatographic techniques. Suitable chromatography techniques include open column or dry column adsorption chromatography, partition chromatography, preparative thin layer chromatography, high pressure liquid chromatography (adsorption or reverse phase), droplet counter-current chromatography, gel permeation chromatography, or ion exchange chromatography.

Suitable adsorbents used in the chromatography include dextran based adsorbents, sephadex such as Sephadex LH-20 or Sephadex G10-G200, silica gel, alumina, polymer beads such as polyamide or polystyrene beads, DEAE cellulose, florisil or magnesol.

In a preferred extraction procedure, about 25 to 75 pounds of the sponge *Pandaros acanthifolium,* which can be obtained from the Caribbean region, such as around the U.S. Virgin Islands or Curacao, are initially extracted with a low MW alcohol such as methanol, ethanol, isopropanol or butanol. This initial extraction is then concentrated in order to remove the alcohol. It is preferable to evaporate the alcohol at a reduced pressure in order to lower the temperature of the boiling solution. The boiling temperature is preferably kept below 50° C. The resulting concentration is extracted step-wise or continuously with the water insoluble organic solvent as discussed above.

One or several portions of each extractant may be used. The concentrate may be extracted with one solvent or with a series of solvents. One preferable series includes methylene chloride or chloroform, then butyl alcohol.

Preparation and Derivatives

Bioactive derivatives of acanthifolic acid of the above formula (I) can be prepared by chemical modification of the carboxyl group or any or all of the multiple OH groups.

The H atom of the hydroxyl group (Q) of the carboxylic acid in the formula of acanthifolic acid may be replaced by a pharmaceutically acceptable cation to form a salt, or by an alkyl group or an aryl group to form an ester. Suitable cations include Na, K, Li, Ca and Mg. Suitable alkyl groups include methyl, ethyl, isopropyl, n-propyl, n-butyl, s-butyl, isobutyl or t-butyl. Suitable aryl groups include phenyl or phenyl substituted by one or more suitable groups such as hydroxy, alkoxy, amino, monosubstituted amino, disubstituted amino, alkyl, aryl, carboxylate, thio and thioalkoxy.

The carboxyl group of acanthifolic acid may be in the form of its amide derivative. The amino group (Q) of the amide may be unsubstituted, monosubstituted or disubstituted. Suitable amino group substituents include alkyl or aryl. Suitable N-alkyl groups include methyl, ethyl, n-propyl, isopropyl, n-butyl, isobutyl, s-butyl or t-butyl. Suitable N-aryl groups include phenyl or phenyl substituted with hydroxy, alkoxy, amino, monosubstituted amino, disubstituted amino, alkyl, aryl, carboxylate, thio and thioalkoxy.

The alcohol groups (where $R_1$, $R_2$, $R_3$ and $R_4 = H$) may be esterified by acyl groups, such as acid groups with from 1 to 5 carbon atoms. Suitable acyl groups include formyl, acetyl, propionyl and benzoyl.

The alcohol groups (where $R_1$, $R_2$, $R_3$ and $R_4 = H$) may also be converted to ethers where $R_1$, $R_2$, $R_3$ and $R_4$ are alkyl or aryl groups. Suitable alkyl groups include methyl, ethyl, propyl, isopropyl, n-butyl, s-butyl, t-butyl and isobutyl. Suitable aryl groups include phenyl and phenyl substituted by hydroxy, alkoxy, amino, monosubstituted amino, disubstituted amino, alkyl, aryl, carboxylate, thio and thioalkoxy.

The alkyl groups of the above-identified esters, ethers and amides may be further functionalized with, for example, additional hydroxyl, amino, or substituted amino groups.

These derivatives of acanthifolic acid may be prepared by the usual procedures. Acanthifolic acid may be converted to various salt derivatives by treating the acid in aqueous alcohol solution with an equivalent of the desired alkali hydroxide and then evaporating and/or lyophilizing the solvent and recrystallizing the residue. Alternatively, the alkali salts of acanthifolic acid may be made by treating a methylene chloride, chloroform, or ethyl acetate solution of the acid with an aqueous solution of the desired alkali carbonate, then drying the organic layer, evaporating the solvent and recrystallizing the residue.

Esters of acanthifolic acid may be made by treating the acid with diazomethane in methanol-benzene or other suitable solvents or by treating the silver salt of acanthifolic acid with appropriate alkyl halides. Alternatively, the following sequence may be used for effecting esterification: (a) reaction of acanthifolic acid with excess t-butyldimethylsiliyl chloride followed by aqueous work-up to convert the alcohol groups to t-butyldimethylsilyl ethers; (b) treatment of the resulting tetraether with oxalyl chloride and pyridine or thionyl chloride and pyridine; (c) reaction of the activated acid group with an appropriate alcohol and finally (d) hydrolysis of the t-butyldimethylsilyl ethers with tetrabutylammonium fluoride in an appropriate aqueous organic solvent.

Amides of acanthifolic acid may be made by using the steps a–d outlined in the previous paragraph, except that in step (c) an appropriate amine will replace an alcohol. Amides may also be made by reacting acanthifolic acid with dicyclohexylcarbodiimide and an amine or appropriately substituted amine in an organic solvent.

Various acyl derivatives of acanthifolic acid, ranging from mono- to tetra-acyl products, may be made by reacting the acid with appropriate acid halides of the general formula RCOX or acid anhydrides [(RCO)$_2$O] in non-hydroxylic organic solvents. Suitable R groups for the acid halides and acid anhydrides include H, methyl, ethyl, propyl, isopropyl, n-butyl, s-butyl, t-butyl or aryl. Acyl derivatives may also be prepared by reacting acanthifolic acid with other acids in the presence of dehydrating agents such as dicyclohexylcarbodiimide. Activated acyl derivatives other than acid halides and anhydrides may also be used.

Ether derivatives of the hydroxyl groups in acanthifolic acid may be made by treatment of the acid with diazoalkanes in methanol-benzene in the presence of silica gel or by reaction of acanthifolic acid or its ester with base and a dialkylsulfate in a suitable solvent such as dimethyl sulfoxide.

Biological Activity

The presently disclosed compounds have cytotoxic and antitumor activity toward mammals. Testing according to National Cancer Institute protocols produced ED$_{50}$ values for acanthifolic acid of $2.8 \times 10^{-4}$ ug/ml toward lymphocytic luekemia P388 in mice, $2.1 \times 10^{-3}$ ug/ml toward human carcinoma of the nasopharynx (KB cell culture); and $3.9 \times 10^{-3}$ ug/ml toward lymphoid leukemia (L1210).

To be considered active by NCI, materials must display an ED$_{50}$ of 20 ug/ml or less. Acanthifolic acid exceeds this requirement by a factor of 10,000 in the P388 screen.

The compounds of the present invention are also useful as antibiotics and are particularly useful in treating poultry coccidiosis, stimulating myocardial contractility or improving the utilization of ruminant feed. Myocardial contractility is stimulated in mammals such as dogs, rabbits, rats and humans.

In order to use the compounds of the present invention as antitumor, cytotoxic or antibiotic agents or to stimulate myocardial contactility or improve the utilization of ruminant feed, the compounds may be used in their substantially pure states or may be combined with suitable pharmaceutical carriers. In such compositions, the purified compounds of this invention can be used in amounts of from 1–99% by weight.

Suitable pharmaceutical carriers include salts such as saline solution, ethyl alcohol, glycols such as ethylene glycol, sugars and topical carriers such as alcohols, cremes, ointments, salves or balms containing suitable ingredients such as oils, fats and the like.

The compound or pharmaceutical composition may be topically applied such as to a tumor or lesion; may be administered orally; interperitoneally or intraveneously.

The compounds are administered in an effective, non-toxic amount, suitably 0.001-100 mg per day per kg of body weight, or suitably 0.001-50 mg per day per kg of body weight.

Having generally described the invention a more complete understanding can be obtained by reference to certain specific examples, which are provided herein for purposes of illustration only and are not intended to be limiting unless otherwise specified.

EXAMPLE 1

Extraction of Acanthifolic Acid from *Pandaros acanthifolium:*

About 20 pounds (wet weight) of *Pandaros acanthifolium* was soaked in 20 l of isoproypl alcohol for two days. The resulting extract was then concentrated at temperatures less than 45° C. under reduced pressure to remove most of the alcohol. The concentrate was extracted in a continuous extractor for three days with 3 l $CH_2Cl_2$. The $CH_2Cl_2$ was then evaporated and the residue dissolved in 250 ml of 90% aqueous methanol. The aqueous methanol was extracted with three portions of hexane (250, 100 and 100 ml, respectively). Enough water (~37 ml) was added to the aqueous methanol to reduce the methanol content to approximately 80%. The aqueous methanol was extracted with three portions of $CCl_4$ (250, 100 and 100 ml, respectively). Enough water (~37 ml) was added to the aqueous methanol fraction to reduce the methanol content to approximately 70%. The aqueous methanol was extracted with three portions of $CHCl_3$ (250, 100 and 100 ml, respectively). The $CCl_4$ and the $CHCl_3$ fractions were combined and chromatographed over a Sephadex LH-20 column (2"×38") using $CHCl_3$—$CH_3OH$ (1:1) as eluant. Approximately 100 ml fractions were collected. The sixth fraction contained a residue of approximately 129 mg, of which 125 mg was chromatographed over 15 gm of tlc mesh silica gel using gradient elution beginning with [benzene-ethyl acetate (1:1)] and progressing to pure $CH_3OH$. Fractions were collected as follows:

| Fraction Number | Solvent (~ 25 ml Fractions) | Eluant |
|---|---|---|
| 1 | Benzene-ethyl acetate (1:1) | 4.2 mg |
| 2 | Benzene-ethyl acetate (1:1) | 1.8 mg |
| 3 | [Benzene-ethyl acetate (1:1)]—$CH_3OH$ (95:5) | 1.9 mg |
| 4 | [Benzene-ethyl acetate (1:1)]—$CH_3OH$ (90:10) | 6.7 mg |
| 5 | [Benzene-ethyl acetate (1:1)]—$CH_3OH$ (80:20) | 8.8 mg |
| 6 | [Benzene-ethyl acetate (1:1)]—$CH_3OH$ (70:30) | 28.2 mg |
| 7 | [Benzene-ethyl acetate (1:1)]—$CH_3OH$ (50:50) | 12.9 mg |
| 8 | $CH_3OH$ | 53.7 mg |

Fraction 6 of this silica gel chromatography was chromatographed over tlc mesh silica gel using gradient elution beginning with [benzene-ethyl acetate (1:1)]—$CH_3OH$ (90:10) and progressing to pure $CH_3OH$. Fractions 3 and 4 were combined and chromatographed over tlc mesh silica gel using [benzene-ethyl acetate (1:1)]—$CH_3OH$ (90:10) as eluant. The first fraction contained 2.2 mg of impure acanthifolic acid, mp 129°-131° C., (decomp.).

The above process was repeated starting with approximately 60 pounds of wet sponge and this yielded 30 mg of crude acanthifolic acid, mp 152°-153° C., $[\alpha]_D+31.5$.

Figure 2:
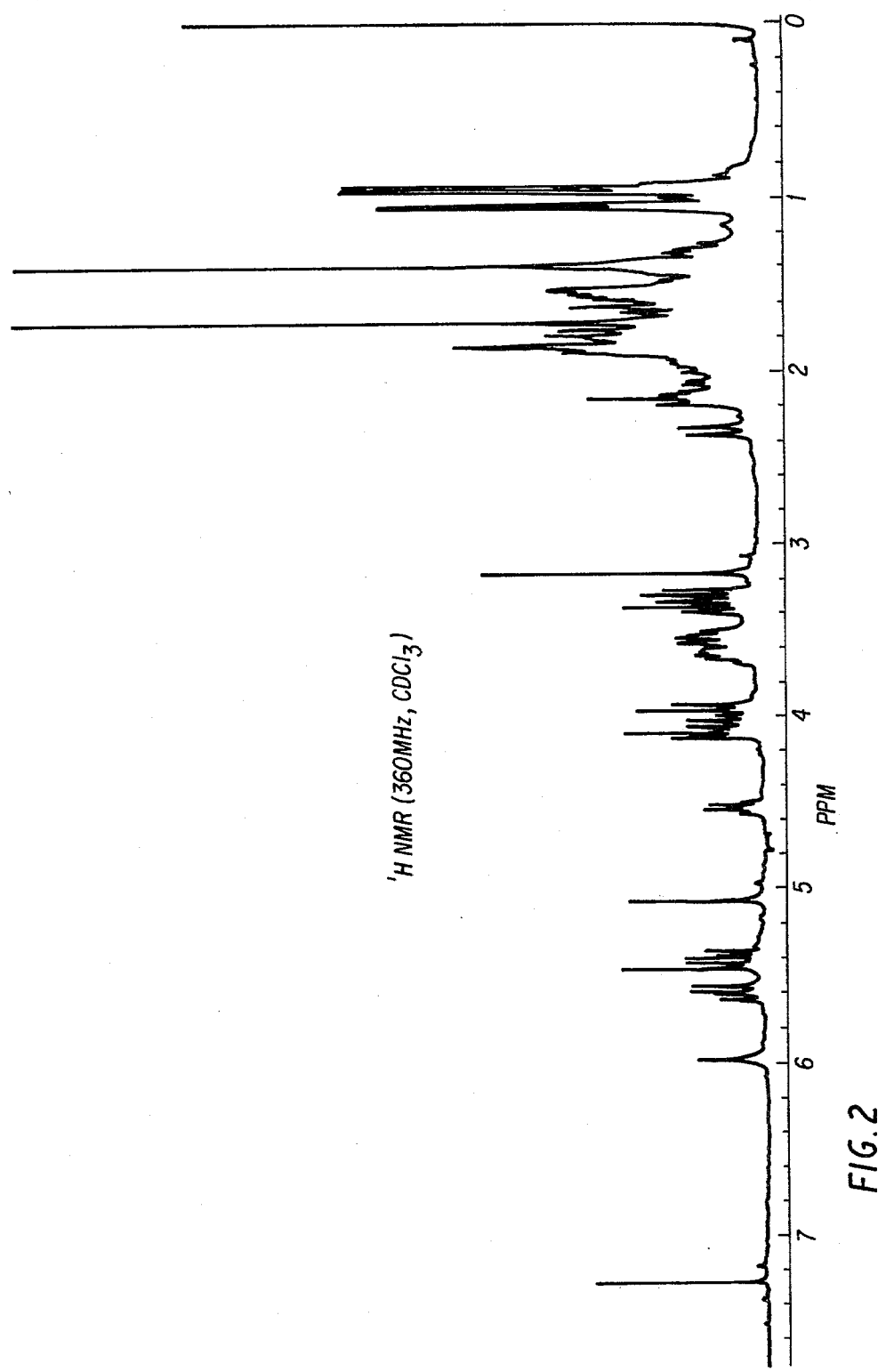
FIG. 2 is a nuclear magnetic resonance spectrum of acanthifolic acid at 360 MHz using $CDCl_3$ as the solvent.

Approximately 10 mg of the above acanthifolic acid was dissolved in a 1:1 mixture of chloroform-benzene, filtered and concentrated, and an open vial containing the resulting solution was placed in a larger closed container containing hexane overnight. The fine white needles that formed were freed of a fine white powder by stirring and removing the solvent with a fine tip pipette, followed by washing with a hexane-benzene mixture in a similar manner. Yield 8.7 mg; mp 162° C. with gas evolution. This solid was recrystallized twice more from chloroformbenzene (1:4) to give pure acanthifolic acid, mp 167°-169° C., $[\alpha]_D+28.3$ (c 0.018, $CHCl_3$). The ir and nmr spectra of pure acanthifolic acid is given in FIGS. 1 and 2.

Determination of Structure by X-ray Diffraction:

The structure was determined by x-ray diffraction.

Long, thin, prismatic crystals of the compound were obtained from benzene/chloroform solution by slow evaporation. A crystal of dimensions 0.55×0.10×0.09 mm was selected for cell measurements and intensity data collection. All x-ray measurements were carried out on an Enraf-Nonius CAD-4 automatic diffractometer controlled by a PDP8/e computer and fitted with a low-temperature device. Orthorhombic symmetry consistent with space group $R2_12_12$ was confirmed by Laue symmetry and systematic absences [hOO, h=2n+1; OkO, k=2n+1]. The crystal data of the compound are: Orthorhombic, $P2_12_12$, a=10.580(3) Å, b=34.594(8) Å, c=14.007(5) Å, V=5126.6 Å$^3$ at −135° C.; Z=4. Intensities of 5881 unique reflections with $2\theta \leq 150°$ were measured at −135(2)°C. using Ni-filtered CuKα radiation and by employing $\theta$-$2\theta$ scan techniques. Out of the total, 4593(78%) reflections were stronger than 1.5 times the standard deviation of their intensities.

The structure of the compound was determined by using the direct methods coupled with the successive difference Fourier syntheses. As the chemical composition of the compound was unknown, each difference Fourier map was carefully scrutinized and atom identifications were made on the basis of both their peak heights and isotropic thermal parameters. The heavy atom (sulfur) was initially refined as oxygen with double occupancy, and later confirmed as sulfur by comparing with the known geometry of episulfides. All refinements were carried out by using a block-diagonal least-squares program. The difference Fourier calculated at the later stage of refinements, indicated the presence of two disordered benzene molecules per asymmetric unit. One of the benzene molecules was included into the refinements, while a badly disordered one was left out. The final R factor for 4332 observed reflections was 0.094. A perspective view of the molecule of acanthifolic acid is shown in FIG. 3. The molecular backbone has a complex shape where one end of it is turned around forming the familiar cavity observed in a number of polyether antibiotics. The cavity has a diameter of 5-7 Å and is held together by an intramolecular hydrogen bond (2.95 Å) between the hydroxyl on ring E and one of the carboxylate oxygens. Ten of the thirteen oxygen atoms in the molecule cluster around this cavity—with seven oxygen atoms within 4.0 Å from its center. The rings F and G are extended out from the cavity region giving the overall molecule a length of about 15 Å. Acanthifolic acid has the unique feature of having an episulfide function and six-membered fused ring system (rings D and E). All five hydroxyl groups are involved in hydrogen bonding (both intra and inter-molecular).

Having now fully described the invention, it will be apparent to one of ordinary skill in the art that many changes and modifications can be made thereto without departing from the spirit or scope of the invention as set forth herein.

What is claimed as new and intended to be covered by letters patent is:

1. A purified bioactive compound of the formula:

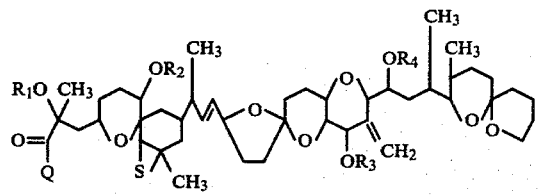

wherein:
Q is selected from the group consisting of OY and $NZ_1Z_2$;
Y is selected from the group consisting of H, alkyl, hydroxyalkyl, aminoalkyl, substituted aminoalkyl, aryl and a pharmaceutically acceptable cation;
$Z_1$ and $Z_2$ are selected from the group consisting of H, alkyl, hydroxyalkyl, aminoalkyl, substituted aminoalkyl, and aryl;
$R_1$, $R_2$, $R_3$ and $R_4$ are selected from the group consisting of H, alkyl, hydroxyalkyl, aminoalkyl, substituted aminoalkyl, aryl and

; and
W is selected from the group consisting of H, alkyl, hydroxyalkyl, aminoalkyl, substituted aminoalkyl and aryl.

2. The compound of claim 1, wherein Q is OY and Y, $R_1$, $R_2$, $R_3$ and $R_4$ represent H.

3. The compound of claim 1, wherein each of said alkyl groups contain between 1 and 4 carbon atoms.

4. A composition containing a cytotoxically or antibiotically effective amount of a compound of the formula:

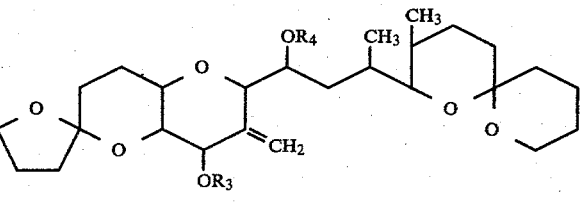

wherein:
Q is selected from the group consisting of OY and $NZ_1Z_2$;
Y is selected from the group consisting of H, alkyl, hydroxyalkyl, aminoalkyl, substituted aminoalkyl, aryl and a pharmaceutically acceptable cation;
$Z_1$ and $Z_2$ are selected from the group consisting of H, alkyl, hydroxyalkyl, aminoalkyl, substituted aminoalkyl and aryl;
$R_1$, $R_2$, $R_3$ and $R_4$ are selected from the group consisting of H, alkyl, hydroxyalkyl, aminoalkyl, substituted aminoalkyl, aryl and

and
W is selected from the group consisting of H, alkyl, hydroxyalkyl, aminoalkyl, substituted aminoalkyl and aryl; in combination with a pharmaceutical carrier.

5. The composition of claim 4, wherein Q is OY and Y, $R_1$, $R_2$, $R_3$ and $R_4$ represent H.

6. The composition of claim 4, wherein each of said alkyl groups contain between 1 and 4 carbon atoms.

* * * * *